United States Patent [19]

Shirkhan

[11] Patent Number: 5,238,556
[45] Date of Patent: Aug. 24, 1993

[54] CHROMATOGRAPHY TUBE FOR USE WITHIN A PRESSURIZED CIRCUIT

[76] Inventor: Hamid Shirkhan, 9 Ronan St., Dorchester, Mass. 02125

[21] Appl. No.: 882,288

[22] Filed: May 13, 1992

[51] Int. Cl.⁵ .............................................. B01D 15/08
[52] U.S. Cl. .................................. 210/198.2; 210/656
[58] Field of Search ................ 210/635, 656, 198.2; 55/386; 422/70

[56] References Cited

U.S. PATENT DOCUMENTS

| | | | |
|---|---|---|---|
| 3,682,315 | 8/1972 | Haller | 210/198.2 |
| 3,810,545 | 5/1974 | Filz | 210/198.2 |
| 3,970,561 | 7/1976 | Sievers | 210/198.2 |
| 4,079,009 | 3/1978 | Seiler | 210/198.2 |
| 4,131,547 | 12/1978 | Michel | 210/198.2 |
| 4,187,177 | 2/1980 | Stahl | 210/198.2 |
| 4,250,035 | 2/1981 | McDonald | 210/198.2 |
| 4,280,905 | 7/1981 | Gunkel | 210/198.2 |
| 4,289,620 | 9/1981 | Hara | 55/386 |
| 4,353,801 | 10/1982 | Mukoyama | 210/198.2 |
| 4,451,364 | 5/1984 | Higgins | 210/198.2 |
| 4,476,017 | 10/1984 | Scharff | 210/198.2 |
| 4,591,442 | 5/1986 | Andrews | 210/656 |
| 4,676,898 | 6/1987 | Saxena | 210/656 |
| 4,727,034 | 2/1988 | Matsushita | 210/649 |
| 4,740,298 | 4/1988 | Andressen | 210/198.2 |
| 4,752,391 | 6/1988 | Porsch | 210/198.2 |
| 4,872,979 | 10/1989 | Goloy | 210/656 |
| 5,011,608 | 4/1991 | Damjanovic | 210/198.2 |
| 5,037,544 | 8/1991 | Snyder | 210/656 |

OTHER PUBLICATIONS

Biochemicals Organic Compounds for Research and Diagnostic Reagents–SIGMA Chemical Company, pp. 1812 through 1818, 1992.
ALDRICH Chemical Catalog-pp. 1549 through 1556, 1992.

*Primary Examiner*—Ernest G. Therkorn
*Attorney, Agent, or Firm*—Weingarten, Schurgin, Gagnebin & Hayes

[57] ABSTRACT

The invention provides a separation column useful for liquid-solid column chromatography. In an exemplary embodiment a polytetrafluorethylene tube is provided which is threaded on each end. Threaded polytetrafluorethylene fittings mate with the threads of the tube, and compress an O-ring on each end of the tube, to form a liquid-tight sealing of the tube under pressurized or non-pressurized use. The threaded polytetrafluorethylene tube may be vacuum packed in a plastic bag with a chromatographic medium retained within the polytetrafluorethylene tube. The chromatographic medium may be formed from one or more layers of chromatographic material. Another embodiment incorporates permeable polytetrafluorethylene discs, known generally as frits, in gravity fed polytetrafluorethylene separation column.

21 Claims, 3 Drawing Sheets

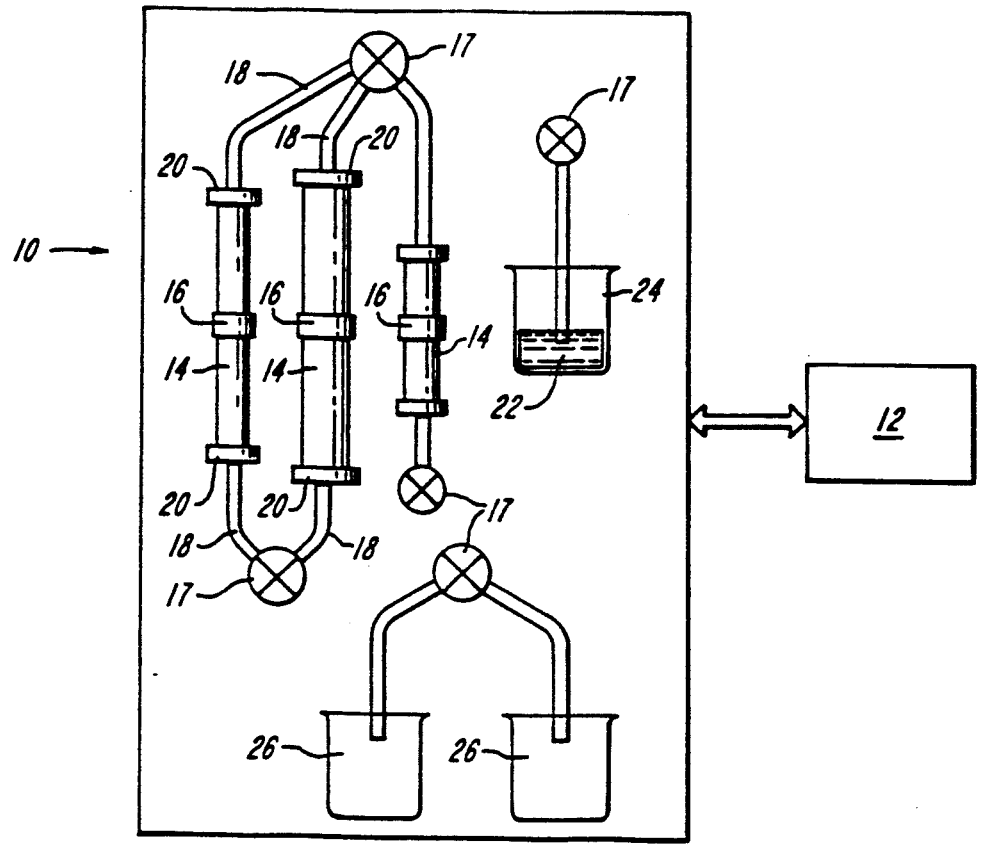
FIG. 1
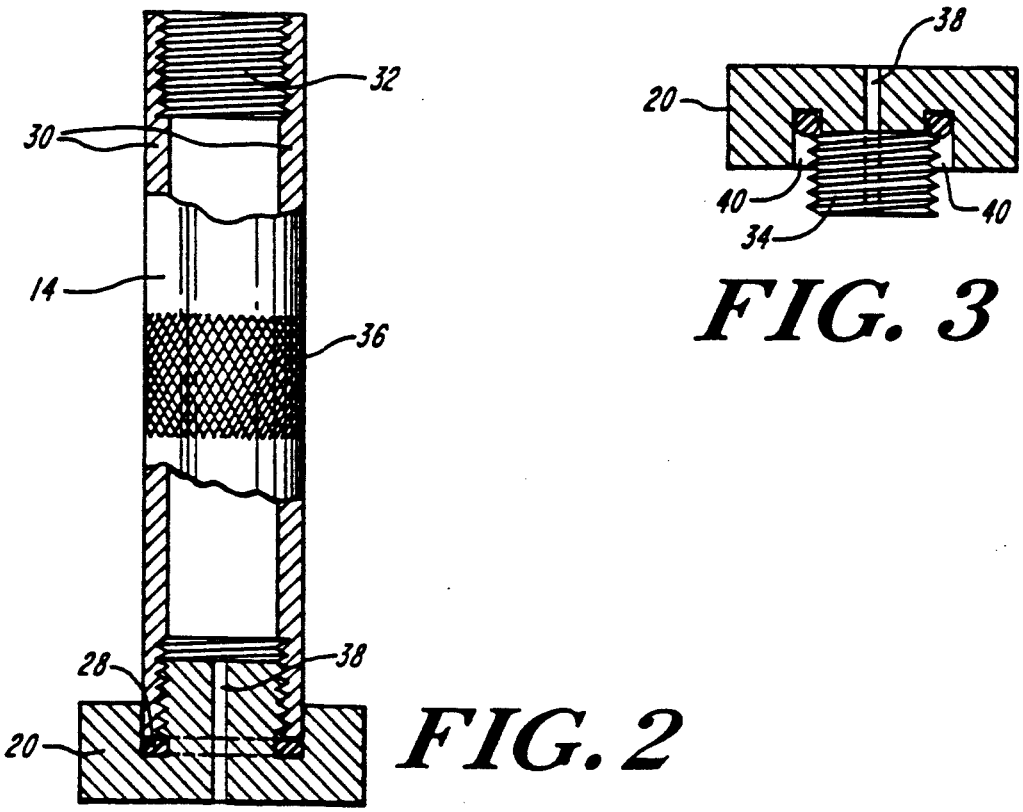
FIG. 2
FIG. 3

CHROMATOGRAPHY TUBE FOR USE WITHIN A PRESSURIZED CIRCUIT

FIELD OF THE INVENTION

This relates to separation columns, and more specifically to a chromatography tube operating at above ambient pressure.

BACKGROUND OF THE INVENTION

Isolation of specific chemical compounds may be accomplished through different separation techniques based on a variety of properties of materials. Among the most commonly used properties are those involving solubility, volatility, adsorption, and electrical and magnetic effects. A common separation method is column chromatography, whereby individual compounds which were originally present in a mixture are resolved from each other by the selective process of distribution between two immiscible phases, such as liquid and solid.

In one form of column chromatography, called permeation chromatography, molecules from a sample are caused to interact physically with the surface of a porous solid by means of adsorption. The adsorptive effect of the chromatographic medium for different solutes determines their rates of migration through the porous medium which is packed in a tube or column. The sample being processed may either flow through the medium under the influence of gravity or under pressure.

To ensure accurate test results, it is generally desirable that the material comprising the column, as well as any fittings in contact with the sample be non-reactive. This is especially important when separating or purifying polychlorinated dibenzo-p-dioxins and polychlorinated dibenzofurans (PCDD/PCDF) from environmental and biological samples.

Prior art techniques for processing samples containing dioxins make use of glass, gravity fed chromatography columns. Attempts have been made to make the columns of plastic, such as polypropylene, but this approach has several drawbacks. Ordinary plastic leaches solvents, thus isolation and identification by chromatographic means of extremely small quantities of dioxin may be compromised. However, plastic is much cheaper than its non-reactive alternative: glass. Glass columns are expensive and difficult to ship and work with due to their fragility.

SUMMARY OF THE INVENTION

In surmounting the disadvantages of prior art separation columns, the invention provides a separation column which may be used under pressure. Features of the invention include a polytetrafluoroethylene tube having threads at each end which mate with polytetrafluoroethylene pressure fittings. The pressure fittings, in combination with polytetrafluoroethylene coated plastic O-rings, ensure a fluid tight seal of the tube when a pressurized liquid test sample is pumped into the tube through an opening in one of the pressure fittings. An opening in the other pressure fitting allows for removal of the fluid from the tube.

Additionally, for ease of use, the tube may be pre-packed with a chromatographic separation medium and permeable polytetrafluoroethylene frits through which the sample must migrate before exiting the tube. The frits hold the separation medium in place within the tube during use and facilitate packing the tube during fabrication. The frits may also separate different chromatographic media into layers if more than one medium is desired. After fabrication, the pre-packed column may be vacuum packaged to prevent contamination and increase shelf life.

Yet another feature of the invention is a polytetrafluoroethylene, gravity fed, separation column having a permeable polytetrafluorethylene frit accessible from an open tube end, yet designed to retain the frit in place and to direct fluid flow to a specific exit point on the column.

BRIEF DESCRIPTION OF THE DRAWINGS

A more complete understanding of the present invention and attendant advantages and features thereof will be more readily understood by reference to the following detailed description when considered in conjunction with the accompanying drawings wherein:

FIG. 1 is a schematic illustration of a chromatography tube in accordance with the present invention connected to an automatic test apparatus;

FIG. 2 is a side sectional view of a polytetrafluorethylene chromatography tube of the invention having interior wall threads and sealed by a fitting on one end;

FIG. 3 is a side sectional view of a polytetrafluorethylene fitting used with the polytetrafluorethylene chromatography tube of FIG. 2;

DETAILED DESCRIPTION OF THE INVENTION

Figure 4:
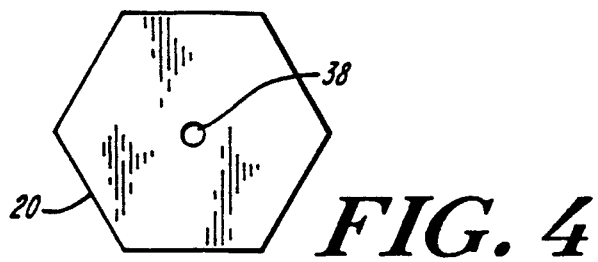
FIG. 4 is a top view of the polytetrafluorethylene fitting of FIG. 3.

Reference is made to the drawings wherein like numerals designate corresponding or similar elements throughout the several views. FIG. 1 is a schematic of an automated test station 10 controlled by a computer 12. Chromatography tubes 14 of various sizes are mounted vertically in holders 16 and are connected to other components of the test station 10, such as control valves 17 by tubing 18. Additional tubing 18 and valves 17 which connect the various system elements are inside or behind the test station 10 and are not shown. The tubing 18 permits pressurized passage of a sample 22 from a sample cup 24 throughout the test station 10 and into the various chromatography tubes 14 through specially adapted fittings or tube end caps 20, and finally into various collection beakers 26 for subsequent analysis.

FIG. 2 is a side sectional view of a representative chromatography tube 14 with one end sealed by a fitting 20 and O-ring 28 fabricated entirely of polytetrafluorethylene. When installed in the test station 10, the tube is packed with a specific separation material and is sealed at both ends. Polytetrafluorethylene, commonly known as Teflon ®, is non-reactive like glass, but is much cheaper to mass produce, is virtually unbreakable and does not leach materials which interfere with the analysis for dioxin or other compounds. However, despite polytetrafluorethylene's desirable characteristics, it typically has not been used in chromatography tubes subjected to pressure because of perceived problems with leakage from the tube due to the material's slippery or non-stick nature. The device described herein has a unique configuration which overcomes the previous inability to use this material for pressurized chromatography.

The tube 14 shown in FIG. 2 has tube walls 30 thick enough to withstand pressurization without bulging, and thick enough to cut or mold threads 32 into. The threads 32 in this illustration are on the interior of the tube walls 30 and are dimensioned so that the polytetrafluorethylene is pliant enough to readily deform when a fitting 20, having complimentary threads 34, is twisted onto the tube 14 by hand. The threads 32, 34 help to seal the tube 14, as well as to ensure a connection between a tube 14 and a fitting 20 subjected to pressurization.

Figure 7:
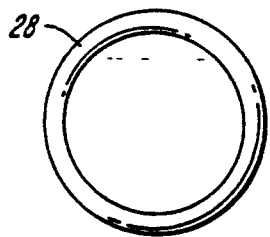
FIG. 7 is plan view of the polytetrafluorethylene O-ring seal of FIGS. 2 and 5.
Figure 7A:
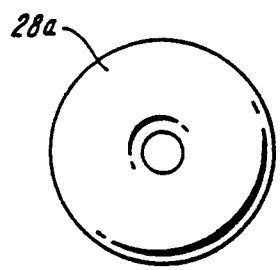
FIG. 7a is a plan view of another polytetrafluorethylene O-ring seal compatible with the embodiment of FIG. 5.

An additional element of the seal is an O-ring 28 which is seated on the end of the tube 14 and squeezed tightly against the fitting 20 as the fitting 20 is twisted into place. The O-ring 28, having a shape better understood with reference to FIG. 7, is made entirely of polytetrafluorethylene or a polytetrafluorethylene coated plastic ring. Various plastics, such as Viton ®, may be used for the O-ring 28 depending on how compressible the ring needs to be to ensure a liquid tight pressure seal, and the O-ring is polytetrafluorethylene coated to ensure its non-reactivity. FIG. 7a depicts another embodiment of the O-ring 28, having a smaller central opening than the O-ring 28 of FIG. 7, and which is useful with the fitting 20 of FIG. 5.

The tube 14 of FIG. 2 is shown with optional knurls 36 on the exterior of the tube walls 30 to render the tube 14 easier to manipulate by hand or with a tool. These knurls 36 may take a variety of forms and be anywhere on the exterior of the tube 14.

FIG. 3 is a side sectional view of the fitting 20 illustrated in FIG. 2 which more clearly reveals the present features of the fitting 20. The fitting 20 is made of polytetrafluorethylene and has threads 34 cut into or molded onto a central portion having a hole or channel 38 which permits a liquid sample 22 to pass through the fitting 20, into, or out of, the tube 14. The channel 38 is designed to receive and hold in place a supply or elution tubing 18. The threads 34 of the fitting 20 are dimensioned like the threads 32 on the tube 14 and are deformable in a similar manner. The fitting 20 also has a recessed area 40 useful for retaining the O-ring 28 which fits snugly against the upper portion of the exterior walls 30 of the tube 14.

FIG. 4 is a top view of the fitting 20 of FIG. 3 in an embodiment having a hexagonal shape. The six flattened sides enable the fitting 20 to be comfortably grasped and turned by hand, and are sized to be compatible with standard wrenches should their use be desired. Many other shapes for the fitting 20 are compatible with the invention as long as they include polytetrafluorethylene construction, an O-ring 28, and threads 34 matable with the threads 32 of the tube 14. One such alternative embodiment is depicted in FIG. 5.

Figure 5:
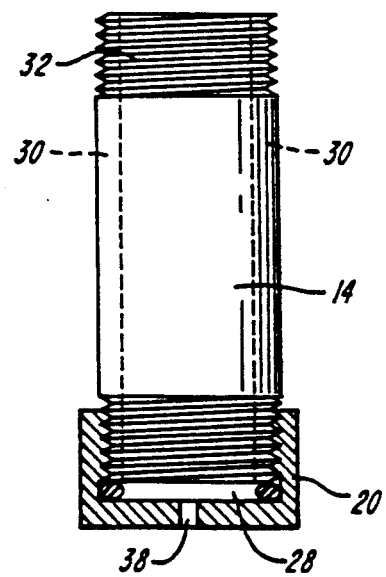
FIG. 5 is a side sectional view of a polytetrafluorethylene chromatography tube of the invention having exterior wall threads and sealed by a fitting on one end.

FIG. 5 illustrates a tube 14 having threads 32 on the exterior of the tube's extremities with a compatible fitting 20 installed on one end. This fitting 20 is shown, in cross-section, at FIG. 6. It is also contemplated that one end of the tube 14 may have interior threads 32 and a fitting 20 like those shown in FIG. 2, while the other end may have exterior threads 32 and a fitting 20 like those shown in FIG. 5.

Figure 8:
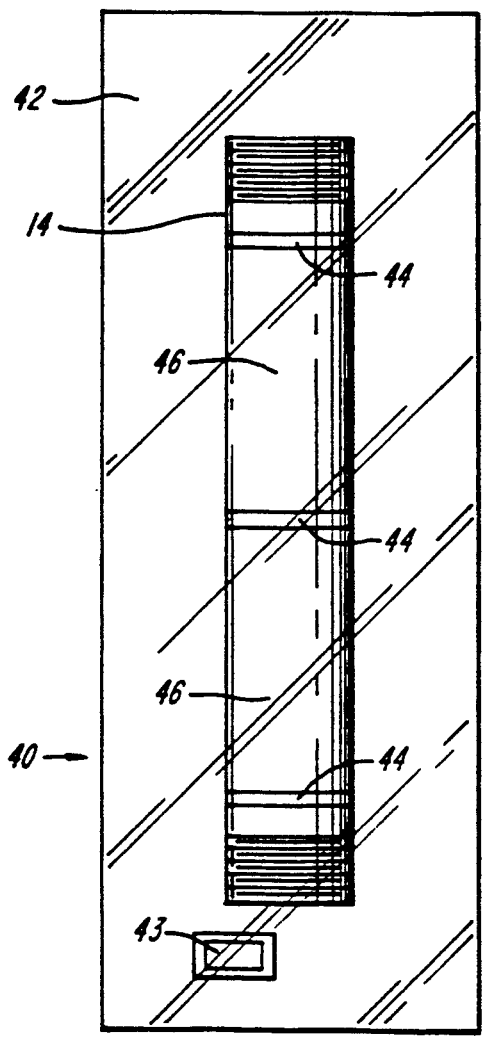
FIG. 8 is side view of the polytetrafluorethylene chromatography tube of the invention pre-packed with a separation medium, frits, and vacuum packaged.

With reference to FIG. 8, a pre-packed chromatography column 40 in accordance with the invention is shown in a vacuum package 42. The column 40 shown is an easy to ship and store, long shelf-life "replacement" column for use in a high-volume laboratory. The column 40 has a tube 14 structure similar to the tubes of FIGS. 2 and 5, and is shown packaged without fittings 20.

The column 40 of FIG. 8 is produced by placing a porous polytetrafluorethylene disc or frit 44 at a predetermined point in the tube 14. The frit 44 has a diameter which is slightly larger or substantially the same as that of the inner tube diameter and is thereby held in a fixed location by compression or friction. Traditional sintered glass frits are also compatible with the invention and may be used in place of, or in combination with, a polytetrafluoroethylene frit 44. The polytetrafluoroethylene frit 44 is rendered more permeable by way of at least one small hole in the frit 44. The exact number and size of the holes in the frit is a function of the inner diameter of the tube 14 and the pressurization level within the tube 14. For example, a tube 14, having a 17/16 inch inner diameter, uses a frit 44, having 8 holes 10-20 microns in diameter, to maintain a 10 milliliter per minute flowrate at 10 pounds per square inch. This number of holes simulates a pore size in the frit 44 of forty microns.

Following installation of the lowermost frit 44, the tube 14 is placed in a vibrating holder (not shown) which permits dry compacting of chromatographic media 46, such as those effective in isolating polychlorinated dibenzo-p-dioxins (e.g. alumina, carbon or silica), which are poured into the tube 14. In lieu of vibratory compaction, mechanical packing by filling and tamping is contemplated. Following compaction, a second frit 44 is placed in the tube against the top of the compacted medium 46.

Figure 6:
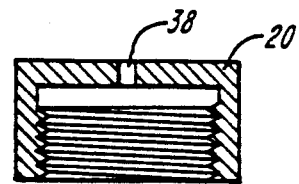
FIG. 6 is a side sectional view of a polytetrafluorethylene fitting used with the polytetrafluorethylene chromatography tube of FIG. 5.

Generally, the compacted medium 46 is held in the portion of the tube 14 bounded by the threads 32. This allows complete entry of the threaded portion of the fitting 20, as depicted in FIG. 3, when the tube 14 and fitting 20 are mated, thereby eliminating dead space within the tube. When a fitting 20, such as that shown in FIG. 6, is mated with the tube, a plug that permits passage of the sample 22 may be inserted into the tube 14 to fill the dead space. In order to compensate for variations in fill level of the tube 14, a piece of plugging material is placed into the tube 14 until it presses against the frit 44; then the plugging material is severed at the opening of the tube 14.

The packing process as described may be performed to produce multiple layers of chromatographic media 46 separated by frits 44. The embodiment of the tube shown in FIG. 8 has two layers of chromatographic media 46 held in place and separated by porous polytetrafluorethylene frits 44. The packed column 40 is then placed into a plastic package 42 and vacuum sealed to prevent contamination. Depending on the medium 46, the column 40 may be sealed in the package 42 with a desiccant 43 to absorb moisture or an inert gas to prevent undesired chemical reactions due to moisture.

When the column 40 thus formed is used in a test station 10, a sample 22 must migrate through the porous polytetrafluorethylene frits 44 and each layer of chromatographic media 46 sequentially before exiting the column 40. Following the test, the column 40 is easily removed from the fittings 20, discarded, and replaced by a new column 40.

Figure 9:
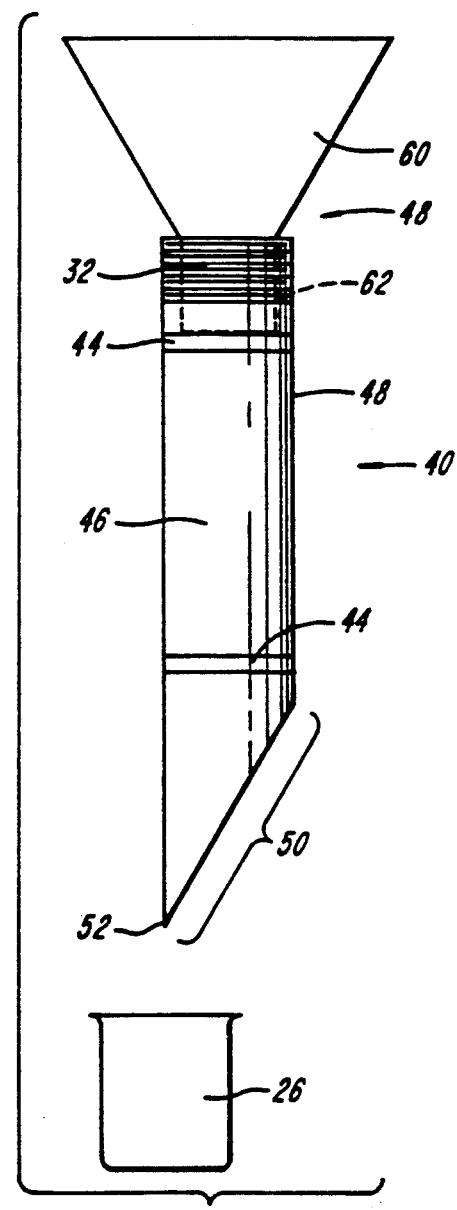
FIG. 9 is a side view of a polytetrafluorethylene, gravity fed chromatography tube incorporating a polytetrafluorethylene frit.

Another embodiment of a chromatographic column 40 is shown in FIG. 9, wherein a polytetrafluorethylene tube 48 is fitted with at least one porous polytetrafluorethylene frit 44, and filled with a chromatographic medium 46. This embodiment is a gravity fed device with the sample 22 being fed into the top of the tube 48 from a sample reservoir 60, migrating through a first frit 44, the medium 46, a second frit 44 and dripping out of the bottom of the tube 48 into a collection cup 26. An angled opening 50 causes the sample 22 to drain from the tube 48 at a lower pointed tip 52, which allows use of small mouthed collection cups 26. The gravity fed column 40 may also be pre-packed and divided into multiple layers by frits 44, as described above with respect to FIG. 8.

Because the gravity fed column 40 generally processes a liquid more slowly than the pressurized columns 40, a reservoir 60 is useful to hold the entire sample 22 until all of it seeps through the frits 44 and the medium 46. The reservoir 60, of FIG. 9, is depicted as a threaded funnel, wherein threads 62 of the reservoir 60 mate with treads 32 of the tube 48. While the reservoir depicted is conically shaped, it may be formed otherwise.

A variety of modifications and variations of the present invention are possible in light of the above teachings. It is therefore to be understood that, within the scope of the appended claims, the present invention may be practiced otherwise than as specifically described hereinabove.

I claim:

1. A polytetrafluorethylene separation column for use in a pressurized circuit comprising:

a polytetrafluorethylene tube open at a first tube end and open at a second tube end, said first tube end having a first lip and a plurality of threads below said lip, and said second tube end having a second lip and a second plurality of threads below said second lip;

a first polytetrafluorethylene pressure fitting comprising a first substantially cylindrical body having a first inner wall, a first outer wall and a first end plug having a first aperture permitting introduction of a liquid into said first tube end, which define a first cavity in said first polytetrafluorethylene pressure fitting for receiving said first tube end for mating, said first inner wall having a third plurality of threads matable with said first plurality of threads which deform when said first polytetrafluorethylene pressure fitting is rotationally tightened onto said first tube end;

a second polytetrafluorethylene pressure fitting comprising a second substantially cylindrical body having a second inner wall, a second outer wall and a second end plug having a second aperture permitting elution of a liquid from said second tube end, which define a second cavity in said second polytetrafluorethylene pressure fitting for receiving said second tube end for mating, said second inner wall having a fourth plurality of threads matable with said second plurality of threads which deform when said second polytetrafluorethylene pressure fitting is rotationally tightened onto said second tube end;

a first O-ring, having at least a polytetrafluorethylene coating, positioned inside said first cavity juxtaposed with said first lip, said first O-ring compressed between said first lip and said first end plug when said first polytetrafluorethylene pressure fitting is rotationally tightened, said first O-ring, said first end plug, and said first and said third plurality of threads creating a liquid tight seal; and a second polytetrafluorethylene coated plastic O-ring positioned inside said second cavity juxtaposed with said second lip, said second polytetrafluorethylene coated plastic O-ring compressed between said second lip and said second end plug when said second polytetrafluorethylene pressure fitting is rotationally tightened, said second polytetrafluorethylene coated plastic O-ring, said second end plug, and said second and said fourth plurality of threads creating a liquid tight seal.

2. The invention of claim 1, wherein said polytetrafluorethylene tube further comprises a first porous polytetrafluorethylene frit, a second polytetrafluorethylene frit, and a chromatographic medium therebetween, said first and said second porous polytetrafluorethylene frit having a substantially identical diameter as an interior tube diameter at a predetermined point, thereby remaining at said predetermined point and retaining said chromatographic medium in a fixed position within said polytetrafluorethylene tube.

3. The invention of claim 2, wherein said first and said second polytetrafluoroethylene frits further comprise a plurality of holes through said frits to increase the porosity of said frits and to maintain a preselected liquid flow rate, at a given pressure, through said frits and said chromatographic medium.

4. The invention of claim 1, said first and said second plurality of threads formed on the exterior of said polytetrafluorethylene tube, said third and said fourth plurality of threads formed on an interior wall of said first and said second polytetrafluorethylene pressure fittings.

5. The invention of claim 4, further comprising a first polytetrafluorethylene plug having a first channel therein for conducting a liquid from said first tube open end to said first porous polytetrafluorethylene frit, and a second polytetrafluorethylene plug having a second channel therein for conducting said liquid from said second porous polytetrafluorethylene frit to said second tube open end.

6. The invention of claim 1, said first and said second plurality of threads formed on the interior of said polytetrafluorethylene tube, said third and said fourth plurality of threads formed on an exterior wall of said first and said second polytetrafluorethylene pressure fittings.

7. The invention of claim 1, said first plurality of threads formed on the interior of said polytetrafluorethylene tube, said second plurality of threads formed on the exterior of said polytetrafluorethylene tube, said third plurality of threads formed on an exterior wall of said first polytetrafluorethylene pressure fitting, and said fourth plurality of threads formed on an interior wall of said second polytetrafluorethylene pressure fitting.

8. The invention of claim 1, said first plurality of threads formed on the exterior of said polytetrafluorethylene tube, said second plurality of threads formed on the interior of said polytetrafluorethylene tube, said third plurality of threads formed on an interior wall of said first polytetrafluorethylene pressure fitting, and said fourth plurality of threads formed on an exterior wall of said second polytetrafluorethylene pressure fitting.

9. The invention of claim 1, wherein a portion of the exterior of said polytetrafluorethylene tube is textured to facilitate handling.

10. The invention of claim 1, wherein said first and said second polytetrafluorethylene pressure fittings have at least two flattened sides to facilitate tightening with a tool.

11. The invention of claim 1, wherein said first O-ring and said second O-ring comprise a compressible plastic substrate coated with polytetrafluorethylene.

12. The invention of claim 1, wherein said first O-ring and said second O-ring are made from a homogeneous piece of deformable polytetrafluorethylene.

13. A pre-packed polytetrafluorethylene separation column comprising:
   a polytetrafluorethylene tube open at a first tube end and a second tube end, said first tube end having a first plurality of threads and said second tube end having a second plurality of threads, said polytetrafluorethylene tube functional within a pressurized circuit;
   a first porous polytetrafluorethylene frit positioned within said polytetrafluorethylene tube at first predetermined position for retaining a chromatographic medium within said polytetrafluorethylene tube;
   a second porous polytetrafluorethylene frit positioned within said polytetrafluorethylene tube at a second predetermined position for retaining a chromatographic medium within said polytetrafluorethylene tube, said first and said second porus polytetrafluorethylene frits having a chromatographic medium therebetween; and
   a vacuum sealed plastic package enclosing said polytetrafluorethylene tube preventing contamination of said chromatographic medium.

14. The invention of claim 13, wherein a desiccant is included inside said vacuum sealed plastic package.

15. The invention of claim 13, wherein said vacuum sealed plastic package includes introduction of an inert gas prior to sealing.

16. The invention of claim 13, wherein said chromatographic medium is compacted into said polytetrafluorethylene tube by Vibration means.

17. The invention of claim 13, wherein said chromatographic medium is compacted into said polytetrafluorethylene tube by tamping.

18. The invention of claim 13, further comprising a first polytetrafluorethylene plug having a first channel therein for conducting liquid from said first tube open end to said first porous polytetrafluorethylene frit, and a second polytetrafluorethylene plug having a second channel therein for conducting said liquid from said second porous polytetrafluorethylene frit to said second tube open end.

19. The invention of claim 13, wherein said first and said second polytetrafluorethylene frits further comprise a plurality of holes through said frits to increase the porosity of said frits and to maintain a preselected liquid flow rate, at a given pressure, through said frits and said chromatographic medium.

20. A pressurized test apparatus comprising:
   at least one intake port for introducing a sample into said pressurized test apparatus;
   at least one exhaust port for voiding said sample form said pressurized test apparatus;
   at least one valve responsive to a control means for time and direction sequencing of said sample through said pressurized test apparatus;
   a separation means for isolating at least one preselected chemical from said sample comprising at least one polytetrafluorethylene separation column comprising:
      a polytetrafluorethylene tube open at a first tube end and open at a second tube end, said first tube end having a first lip and a plurality of threads below said lip and said second tube end having a second lip and a second plurality of threads below said second lip;
      a first polytetrafluorethylene pressure fitting comprising a first substantially cylindrical body having a first inner wall, a first outer wall and a first end plug having a first aperture permitting introduction of a liquid into said first tube end, which define a first cavity in said first polytetrafluorethylene pressure fitting for receiving said first tube end for mating, said first inner wall having a third plurality of threads matable with said first plurality of threads which deform when said first polytetrafluorethylene pressure fitting is rotationally tightened onto said first tube end;
      a second polytetrafluorethylene pressure fitting comprising a second substantially cylindrical body having a second inner wall, a second outer wall and a second end plug having a second aperture permitting elution of a liquid from said second tube end, which define a second cavity in said second polytetrafluorethylene pressure fitting for receiving said second tube end for mating, said second inner wall having a fourth plurality of threads matable with said second plurality of threads which deform when said second polytetrafluorethylene pressure fitting is rotationally tightened onto said second tube end;
      a first O-ring having at least a polytetrafluorethylene coating positioned inside said first cavity juxtaposed with said first lip, said first O-ring compressed between said first lip and said first end plug when said first polytetrafluorethylene pressure fitting is rotationally tightened, said first O-ring, said first end plug, and said first and said third plurality of threads creating a liquid tight seal; and
      a second O-ring having at least a polytetrafluorethylene coating positioned inside said second cavity juxtaposed with said second lip, said second O-ring compressed between said second lip and said second end plug when said second polytetrafluorethylene pressure fitting is rotationally tightened, said second O-ring, said second end plug, and said second and said fourth plurality of threads creating a liquid tight seal; and
   a plurality of tubes connecting said at least one valve to said at least one intake port, said separation means, and said at least one exhaust port.

21. The invention of claim 20, wherein at least one of said polytetrafluorethylene separation columns further comprises a first porous polytetrafluorethylene frit, a second polytetrafluorethylene frit, and a chromatographic medium therebetween, said first and said second porous polytetrafluorethylene frit having a substantially identical diameter as an interior tube diameter at a predetermined point, thereby remaining at said predetermined point and retaining said chromatographic medium in a fixed position within said polytetrafluorethylene tube.

* * * * *